(12) United States Patent
Hannemann et al.

(10) Patent No.: US 11,388,528 B2
(45) Date of Patent: Jul. 12, 2022

(54) METHOD FOR OPERATING A HEARING INSTRUMENT AND HEARING SYSTEM CONTAINING A HEARING INSTRUMENT

(71) Applicant: SIVANTOS PTE. LTD., Singapore (SG)

(72) Inventors: Ronny Hannemann, Buckenhof (DE); Ulrich Giese, Fuerth (DE); Marko Lugger, Weilersbach (DE); Homayoun Kamkar-Parsi, Erlangen (DE)

(73) Assignee: Sivantos Pte. Ltd., Singapore (SG)

( * ) Notice: Subject to any disclaimer, the term of this patent is extended or adjusted under 35 U.S.C. 154(b) by 447 days.

(21) Appl. No.: 16/654,126

(22) Filed: Oct. 16, 2019

(65) Prior Publication Data

US 2020/0120431 A1 Apr. 16, 2020

(30) Foreign Application Priority Data

Oct. 16, 2018 (EP) ..................................... 18200844

(51) Int. Cl.
*H04R 25/00* (2006.01)
*A61B 5/11* (2006.01)
(Continued)

(52) U.S. Cl.
CPC ....... *H04R 25/505* (2013.01); *A61B 5/02055* (2013.01); *A61B 5/11* (2013.01);
(Continued)

(58) Field of Classification Search
CPC ......... H04R 25/505; A61B 5/11; A61B 5/165; A61B 5/4803; A61B 5/02055; G10L 25/63; G10L 25/78; G10L 25/90
(Continued)

(56) References Cited

U.S. PATENT DOCUMENTS 8,386,257 B2 2/2013 Irie et al.
9,363,614 B2 6/2016 Jepsen et al.
(Continued)

FOREIGN PATENT DOCUMENTS

CN 105580389 A 5/2016
CN 105765654 A 7/2016
(Continued)

*Primary Examiner* — Thjuan K Addy
(74) *Attorney, Agent, or Firm* — Laurence A. Greenberg; Werner H. Stemer; Ralph E. Locher (57) ABSTRACT

A method operates a hearing system which has a hearing instrument worn in an ear. The method includes capturing a sound signal from an environment, processing the captured sound signal in dependence of a set of signal processing parameters, and outputting a processed sound signal to the user. The method further includes analyzing the captured sound signal to recognize own-voice intervals, in which the user speaks, analyzing the captured sound signal for an acoustic feature of the own voice of the user and/or analyzing a signal of a bio sensor. The bio sensor measures at least one non-acoustic vital function of the user and determines, from the acoustic feature and/or the non-acoustic vital function of the user, a measure of an emotional state of the user. A value of a signal processing parameter is adapted, within the own-voice intervals, to change the emotional state if a criterion is fulfilled.

12 Claims, 4 Drawing Sheets

(51) Int. Cl.

| | | |
|---|---|---|
| *A61B 5/16* | (2006.01) | |
| *A61B 5/00* | (2006.01) | |
| *G10L 25/63* | (2013.01) | |
| *G10L 25/78* | (2013.01) | |
| *G10L 25/90* | (2013.01) | |
| *A61B 5/0205* | (2006.01) | |
| *A61B 5/145* | (2006.01) | |
| *A61B 5/369* | (2021.01) | |
| *A61B 5/389* | (2021.01) | |
| *A61B 5/021* | (2006.01) | |
| *A61B 5/024* | (2006.01) | |

(52) U.S. Cl.
CPC .......... *A61B 5/14542* (2013.01); *A61B 5/165* (2013.01); *A61B 5/369* (2021.01); *A61B 5/389* (2021.01); *A61B 5/4803* (2013.01); *A61B 5/6815* (2013.01); *G10L 25/63* (2013.01); *G10L 25/78* (2013.01); *G10L 25/90* (2013.01); *H04R 25/407* (2013.01); *A61B 5/021* (2013.01); *A61B 5/024* (2013.01); *H04R 25/405* (2013.01); *H04R 2225/43* (2013.01)

(58) Field of Classification Search
USPC .................................. 381/313, 312, 328, 330
See application file for complete search history.

(56) References Cited

U.S. PATENT DOCUMENTS

| | | | |
|---|---|---|---|
| 9,936,308 | B2 | 4/2018 | Harczos |
| 10,206,049 | B2 | 2/2019 | Ungstrup |
| 10,284,965 | B2 | 5/2019 | Aschoff |
| 10,356,534 | B2 | 7/2019 | Oetting et al. |
| 10,575,106 | B1* | 2/2020 | Bergmann ........... H04R 25/505 |
| 2014/0321682 | A1 | 10/2014 | Kofod-Hansen et al. |
| 2016/0210407 | A1* | 7/2016 | Hwang .............. G06K 9/00496 |
| 2017/0027812 | A1 | 2/2017 | Hyde et al. |
| 2017/0127193 | A1* | 5/2017 | Husung ................ A61B 5/6815 |
| 2017/0361099 | A1 | 12/2017 | De Ridder |

FOREIGN PATENT DOCUMENTS

| | | |
|---|---|---|
| CN | 106063295 A | 10/2016 |
| CN | 107454536 A | 12/2017 |
| CN | 107534820 A | 1/2018 |
| DE | 102009043775 A1 | 4/2011 |
| EP | 2063416 A1 | 5/2009 |
| JP | 2005345496 A | 12/2005 |
| JP | 2014232905 A | 12/2014 |

\* cited by examiner

METHOD FOR OPERATING A HEARING INSTRUMENT AND HEARING SYSTEM CONTAINING A HEARING INSTRUMENT

CROSS-REFERENCE TO RELATED APPLICATION

This application claims the priority, under 35 U.S.C. § 119, of European application EP 18200844.1, filed Oct. 16, 2018; the prior application is herewith incorporated by reference in its entirety.

BACKGROUND OF THE INVENTION

Field of the Invention

The invention relates to a method for operating a hearing instrument. The invention further relates to a hearing system containing a hearing instrument.

A hearing instrument is an electronic device configured to support the hearing of person wearing it (which person is called the "user" or "wearer"). A hearing instrument may be specifically configured to compensate for a hearing loss of a hearing-impaired user. Such hearing instruments are also called "hearing aids". Other hearing instruments are configured to fit the needs of normal hearing persons in special situations, e.g. sound-level-reducing hearing instruments for musicians, etc.

Hearing instruments are typically configured to be worn in or at the ear of the user, e.g. as an in-the-ear (ITE) device or a behind-the-ear (BTE) device. With respect to its internal structure, a hearing instrument normally contains an (acousto-electrical) input transducer, a signal processor and an output transducer. During operation of the hearing instrument, the input transducer captures a sound signal from an environment of the hearing instrument and converts it into an input audio signal (i.e. an electrical signal transporting sound information). In the signal processor, the input audio signal is processed, in particular amplified dependent on frequency. The signal processor outputs the processed signal (also called output audio signal) to the output transducer. Most often, the output transducer is an electro-acoustic transducer (also called "receiver") that converts the output audio signal into a processed sound signal to be emitted into the ear canal of the user.

The term "hearing system" denotes an assembly of devices and/or other structures providing functions required for the normal operation of a hearing instrument. A hearing system may consist of a single stand-alone hearing instrument. As an alternative, a hearing system may contain a hearing instrument and at least one further electronic device which may be, e.g., one of another hearing instrument for the other ear of the user, a remote control and a programming tool for the hearing instrument. Moreover, modern hearing systems often contain a hearing instrument and a software application for controlling and/or programming the hearing instrument, which software application is or can be installed on a computer or a mobile communication device such as a mobile phone (smartphone). In the latter case, typically, the computer or the mobile communication device is not a part of the hearing system. Instead, the computer or the mobile communication device is only used by the hearing system as a resource providing computing power and memory. In particular, most often, the computer or the mobile communication device is a general purpose device that will be manufactured and sold independently of the hearing system.

Generally, the signal processing in modern hearing instruments is controlled by a large number of signal processing parameters that must be adapted to the needs of the individual user to ensure a good benefit of the hearing instrument. This adaptation process, also called "fitting" is a difficult task, due to the diversity of the objective and subjective factors that influence the subjective benefit of a hearing instrument, and thus, the user satisfaction. A specific problem is that the subjective (perceived) benefit of a hearing instrument significantly depends on the emotional state of the user.

SUMMARY OF THE INVENTION

An object of the present invention is to provide a method for operating a hearing instrument being worn in or at the ear of a user which method allows for a particularly good benefit of the hearing instrument to the user.

Another object of the present invention is to provide a hearing system containing a hearing instrument to be worn in or at the ear of a user which system allows for a particularly good benefit of the hearing instrument to the user.

According to a first aspect of the invention, a method for operating a hearing instrument that is worn in or at the ear of a user is provided. The method includes capturing a sound signal from an environment of the hearing instrument, processing the captured sound signal in dependence of a set of signal processing parameters, and outputting a processed sound signal to the user. The method further contains the below described steps.

In an own voice recognition step, the captured sound signal is analyzed to recognize own-voice intervals, in which the user speaks.

In an analysis step, the captured sound signal is analyzed for at least one acoustic feature of the own voice of the user. Alternatively or additionally, a signal of at least one bio sensor is analyzed, the signal being representative of at least one non-acoustic vital function of the user measured by the bio sensor. The term "non-acoustic vital function" generally denotes a function of the body of the user that is not related to the own voice of the user; in particular, the at least one non-acoustic vital function may be selected from at least one of the pulse frequency, the oxygen content of the blood, the blood pressure, the brain activity, a motion of the user (in particular an amplitude and/or frequency of movements of user's head), the skin conductivity or the body temperature. The at least one bio sensor may be integrated in the hearing instrument or be located externally to the hearing instrument (or even externally to a hearing system comprising the hearing instrument), e.g. in an external device such as a smart watch or a mobile phone.

In an embodiment of the invention, the analysis step is performed during recognized own-voice intervals only. In particular, of course, the at least one acoustic feature of the own voice can only be determined during own-voice intervals. However, if applicable, the signal of the at least one bio sensor may also be analyzed outside the own-voice intervals.

In a so-called reduction step, the information contained in the at least one acoustic feature of the own voice of the user and/or the signal of the at least one bio sensor is reduced to a measure of an emotional state of the user. In other words, the measure of the emotional state of the user is determined from the at least one acoustic feature of the own voice of the user and/or the at least one non-acoustic vital function of the user (i.e. the signal of the at least one bio sensor).

The "measure" (or estimate) of the emotional state of the user is an information characterizing the emotional state of the person wearing the hearing instrument. In simple yet effective embodiments of the invention, the measure is configured to characterize the emotional state in a quantitative manner indicating a predefined valence of the emotional state (e.g. in the sense of better/more positive or worse/more negative). For instance, the measure may be provided as a numeric variable, the value of which may vary between a minimum (e.g. "0" corresponding to a very negative emotional state) and a maximum (e.g. "10" corresponding to a very positive emotional state). In other embodiments of the invention, the measure is configured to characterize the emotional state of the user in a qualitative manner. E.g. the measure may be provided as a variable that may assume different values corresponding to "happiness", "activity", "stress", "fatigue", "sadness", "passivity", etc. In more differentiated embodiments of the invention, the measure may be configured to characterize the emotional state of the user in a both qualitative and quantitative manner. For instance, the measure may be provided as a vector or array having a plurality of elements corresponding, e.g., to "activity/passivity", "happiness/sadness", etc., where each of the elements may assume different values between a respective minimum and a respective maximum.

In an embodiment of the present invention, the measure of the emotional state is only recorded for later use, e.g. as a part of a data logging function. Additionally or alternatively, the measure may be provided to the user. However, in a preferred embodiment of the invention, the measure is used to actively change (in particular improve) the emotional state of the user. To this end, in a testing step, the measure of the emotional state is tested with respect to a predefined criterion. By preference, the criterion is defined as to indicate a negative emotional state, i.e. an emotional state to be changed (which may also be an over-positive emotional state such as hyperactivity).

The testing step is followed by an adaptation step, in which a value of at least one of the signal processing parameters is adapted within the own-voice intervals, if the criterion is found to be fulfilled. Adaptation within the own-voice intervals means that the adapted parameter settings are applied to the signal processing during own-voice-intervals so that the adapted parameters selectively control the processing of temporal sections of the captured sound signal that contain the user's own voice. Outside own-voice intervals, different parameter settings may (and, preferably, will) be applied to the signal processing. In particular, preferred embodiments of the method according to the invention do not influence the signal processing outside own-voice intervals.

Preferably, only a given subset of all signal processing parameters of the hearing instrument is selected for adaptation in the adaptation step. Preferred signal processing parameters to be included in the subset are detailed below. In an advantageous embodiment, the values of the selected signal processing parameters are slowly adapted, e.g. using a fading mechanism, so that the adaptation is imperceptible to the user.

The invention is based on the finding that, at the one hand, the own voice of a person is indicative of this person's emotional state, and that, on the other hand, the emotional state of a person is significantly influenced by how this person perceives the own voice. Thus, the perception of a person's own voice constitutes a feedback mechanism that may both stabilize and destabilize the emotional state. By determining and, preferably, changing the emotional state by altering the processing of the own voice in the hearing instrument, the method according to the invention allows to particularly well adapt the hearing instrument to the needs of the individual user. Thus, the benefit of a hearing instrument to the user may be optimized in an efficient manner.

In a preferred embodiment of the invention, the method is configured in the way of a closed-loop control circuit. In this embodiment, the criterion contains a desired value of the measure of the emotional state. Herein, in the testing step, a deviation of the measure of the emotional state with respect to the desired value is determined. In this embodiment, the criterion is fulfilled if the measure (significantly) deviates from the desired value, i.e. if the deviation is non-zero or exceeds a predetermined threshold. In this case, in the adaptation step, the value of the at least one of the signal processing parameters is adapted so that the deviation is reduced, in particular minimized. Preferably, the reduction or minimization is performed in an iterative process, i.e. value of the at least one of the signal processing parameters is adapted repeatedly in a plurality of iterations to successively reduce the deviation. Adapted values of the least one of the signal processing parameters may be calculated using a conventional optimization method, e.g. a Gradient Descent method.

In a more enhanced embodiment of the invention, the captured sound signal is further analyzed for at least one of the following environmental acoustic features:

the (total) sound level of the captured sound signal (including voice and noise);

the noise level or the signal-to-noise ratio;

the reverberation time; and the presence of speakers different from the user.

In this embodiment, the measure of the emotional state is determined in further dependence of the at least one environmental acoustic feature and/or a temporal variation thereof. Considering the at least one environmental acoustic feature allows for a better evaluation of the emotional state. Thus, in particular, the probability of a wrong estimation of the emotional state of the user can be reduced.

According to a second aspect of the invention, a method for operating a hearing instrument that is worn in or at the ear of a user is provided. The method contains capturing a sound signal from an environment of the hearing instrument, processing the captured sound signal in dependence of a set of signal processing parameters, and outputting a processed sound signal to the user.

The method according to the second aspect of the invention further includes:

analyzing the captured sound signal to recognize own-voice intervals, in which the user speaks;

analyzing the captured sound signal for at least one acoustic feature of the own voice of the user and/or analyzing a signal of at least one bio sensor, the bio sensor measuring at least one non-acoustic vital function of the user;

testing the at least one acoustic feature of the own voice of the user and/or the at least one non-acoustic vital function of the user (i.e. the signal of the at least one bio sensor), with respect to a predefined criterion; and adapting a value of at least one of the signal processing parameters, in the own-voice intervals, to change the emotional state if the criterion is fulfilled.

The method according to the second aspect of the invention contains the own-voice-recognition step and the analysis step as described with respect to the first embodiment of the invention. However, the reduction step is missing (i.e. no measure or estimate of the emotional state of the user is explicitly determined). Instead, in modified testing and adaptation steps, the value of the at least one of the signal processing parameters is adapted in direct dependence of the at least one acoustic feature of the own voice and/or the at least one non-acoustic vital function. Again, preferably, the values of the selected signal processing parameters are slowly adapted, e.g. using a fading mechanism, so that the adaptation is imperceptible to the user.

Similar to embodiments of the first aspect of the invention described above, the method according to the second aspect may be configured in the way of a closed-loop control circuit. To this end, the criterion preferably contains respective desired values of the at least one acoustic feature of the own voice of the user and/or the at least one vital function of the user. Here, the testing includes determination of a deviation of the at least one acoustic feature of the own voice of the user and/or the at least one vital function of the user with respect to the desired value. In the adaptation step, the value of the at least one of the signal processing parameters is adapted so that the deviation is reduced, in particular minimized.

Preferably, the method according to the second aspect of the invention includes analyzing the captured sound signal for at least one environmental acoustic feature as disclosed above and testing the at least one environmental acoustic feature with respect to the predefined criterion.

In preferred embodiments of the first or second aspect of the invention, the at least one signal processing parameter (that is adapted in the adaptation step) is selected from at least one of:
a parameter of a noise reduction algorithm;
a parameter of an algorithm adapting the pitch (i.e. the fundamental frequency) of the captured sound signal including the user's own voice; in particular, the algorithm may be operable to effect a shift or inflection of the pitch;
a parameter of an algorithm adapting (i.e. compressing or expanding) the dynamic range of the captured sound signal including the user's own voice;
a parameter for switching between binaural or monoaural sound processing (if the hearing instrument interacts with a second hearing instrument in a binaural hearing system);
a parameter of a beamforming algorithm, i.e. a parameter controlling the directionality of the captured sound signal; and
a parameter of an algorithm adapting the spectral energy of the captured sound signal, e.g. a high pass filter.

In further embodiments of the first or second aspect of the invention, the at least one acoustic feature of the own voice of the user (for which the captured sound signal is analyzed in the analysis step) is selected from at least one of:
the voice level of the own voice,
the formant frequencies of the own voice,
the pitch (fundamental frequency) of the own voice,
the frequency distribution of the own voice, and
the speed or rhythm of speech.

Preferably, the at least one of non-acoustic vital function of the user measured by the at least one bio sensor is selected from at least one of:
the pulse frequency,
the oxygen content of the blood,
the blood pressure,
the brain activity,
muscle activity,
a motion of the user, in particular frequency and/or amplitude of head movements of the user,
the skin conductivity, and
the body temperature.

According to a third aspect of the invention, a hearing system with a hearing instrument to be worn in or at the ear of a user is provided. The hearing instrument contains:
an input transducer arranged to capture a sound signal from an environment of the hearing instrument;
a signal processor arranged to process the captured sound signal in dependence of a set of signal processing parameters; and
an output transducer arranged to emit a processed sound signal into an ear of the user.

In particular, the input transducer converts the sound signal into an input audio signal that is fed to the signal processor, and the signal processor outputs an output audio signal to the output transducer which converts the output audio signal into the processed sound signal.

Generally, the hearing system according to third aspect of the invention is configured to automatically perform the method according to the first aspect of the invention. To this end, the system contains a voice recognition unit that is configured to analyze the captured sound signal to recognize the own-voice intervals. The system further contains an analysis unit that is configured to analyze the captured sound signal for at least one acoustic feature of the own voice of the user and/or to analyze a signal of at least one bio sensor (which may or may not be a part the hearing system), wherein the bio sensor measures at least one non-acoustic vital function of the user. The system further contains a control unit that is configured to determine, from the at least one acoustic feature of the own voice of the user and/or said at least one non-acoustic vital function of the user, a measure of an emotional state of the user as specified above.

Preferably, the control unit is further configured:
to test the measure of the emotional state with respect to a predefined criterion as specified above; and
to adapt a value of at least one of the signal processing parameters to change the emotional state if said criterion is fulfilled.

According to a fourth aspect of the invention, a hearing system with a hearing instrument to be worn in or at the ear of a user is provided. The hearing instrument contains an input transducer, a signal processor and an output transducer as specified above. Herein, the system is configured to automatically perform the method according to the second aspect of the invention. In particular, the system contains a voice recognition unit that is configured to analyze the captured sound signal to recognize said own-voice intervals. The system further contains an analysis unit that is configured to analyze the captured sound signal for at least one acoustic feature of the own voice of the user and/or to analyze a signal of at least one bio sensor (which may or may not be a part the hearing system), wherein the bio sensor measures at least one non-acoustic vital function of the user. The system further contains a control unit that is configured to test the at least one acoustic feature of the own voice of the user and/or the at least one non-acoustic vital function of the user with respect to a predefined criterion as specified above, and to adapt a value of at least one of the signal processing parameters to change the emotional state if the criterion is fulfilled.

Preferably, the signal processor according to the third and fourth aspect of the invention is configured as a digital electronic device. It may be a single unit or consist of a plurality of sub-processors. The signal processor or at least one of the sub-processors may be a programmable device (e.g. a microcontroller). In this case, the functionality mentioned above or part of the functionality may be implemented as software (in particular firmware). Also, the signal processor or at least one of the sub-processors may be a non-programmable device (e.g. an ASIC). In this case, the functionality mentioned above or part of the functionality may be implemented as hardware circuitry.

In a preferred embodiment of the invention, the voice recognition unit according to the third and fourth aspect of the invention is arranged in the hearing instrument. In particular, it may be a hardware or software component of the signal processor. In a preferred embodiment, it contains an own voice detection (OVD) module for detection of the user's own voice and, optionally, a voice activity detection (VAD) module for general voice detection. However, in other embodiments of the invention, the voice recognition unit or at least a functional part thereof may be located in an external electronic device. Optionally, the voice recognition unit may comprise a software component for recognizing a foreign voice (i.e. a voice of a speaker different from the user) that may be implemented as a part of a software application to be installed on an external communication device (e.g. a computer, a smartphone, etc.).

Preferably, the analysis unit according to the third and fourth aspect of the invention is arranged in the hearing instrument, e.g. as a hardware or software component of the signal processor. Alternatively, at least a functional part of the analysis unit may also be configured as a part of a software application to be installed on an external communication device (e.g. a computer, a smartphone, etc.).

The control unit according to the third and fourth aspect of the invention may be arranged in the hearing instrument, e.g. as a hardware or software component of the signal processor. However, preferably, the control unit is arranged as a part of a software application to be installed on an external communication device (e.g. a computer, a smartphone, etc.).

All embodiments of the methods according to the first and second aspect of the invention correspond to matching embodiments of the hearing system according to the third and fourth aspect of the invention, respectively, and vice versa.

Other features which are considered as characteristic for the invention are set forth in the appended claims.

Although the invention is illustrated and described herein as embodied in a method for operating a hearing instrument and a hearing system containing a hearing instrument, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Like reference numerals indicate like parts, structures and elements unless otherwise indicated.

Figure 1:
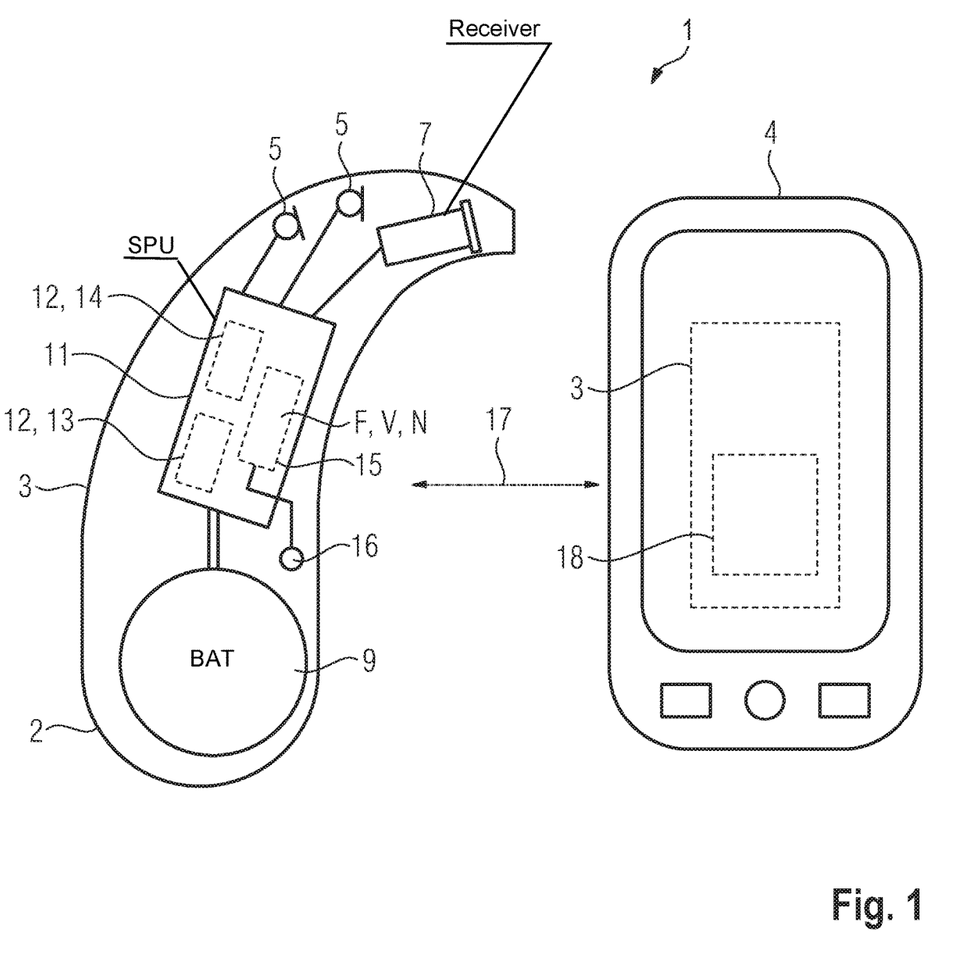
FIG. 1 is a schematic representation of a hearing system containing a hearing aid to be worn in or at the ear of a user and a software application for controlling and programming the hearing aid, the software application being installed on a smartphone.

Referring now to the figures of the drawings in detail and first, particularly to FIG. 1 thereof, there is shown a hearing system 1 containing a hearing aid 2, i.e. a hearing instrument being configured to support the hearing of a hearing impaired user, and a software application (subsequently denoted "hearing app" 3), that is installed on a smartphone 4 of the user. Here, the smartphone 4 is not a part of the system 1. Instead, it is only used by the system 1 as a resource providing computing power and memory. Generally, the hearing aid 2 is configured to be worn in or at one of the ears of the user. As shown in FIG. 1, the hearing aid 2 is configured as a Behind-The-Ear (BTE) hearing aid.

Optionally, the system 1 contains a non-illustrated second hearing aid to be worn in or at the other ear of the user to provide binaural support to the user. In the latter case, both the hearing aid 2 and the other hearing aid are wirelessly connected for exchange of audio signals to perform binaural signal processing.

The hearing aid 2 contains two microphones 5 as input transducers and a receiver 7 as output transducer. The hearing aid 2 further contains a battery 9 and a (digital) signal processor 11. Preferably, the signal processor 11 contains both a programmable sub-unit (such as a microprocessor) and a non-programmable sub-unit (such as an ASIC). The signal processor 11 includes a voice recognition unit 12, that contains a voice activity detection (VAD) module 13 and an own voice detection (OVD) module 14. By preference, both modules 13 and 14 are configured as software components being installed in the signal processor 11. The signal processor 11 also includes an analysis unit 15, which may be configured as a software module or a hardware circuit. Optionally, the hearing aid 2 contains a bio sensor 16 measuring a non-acoustic vital function of the user, e.g. a pulse sensor for measuring the user's pulse or an acceleration sensor for measuring the user's motion. In the latter case, the bio sensor 16 may be used to detect head movements the amplitude and/or frequency may be evaluated by the analysis unit 15.

During operation of the hearing aid 2, the microphones 5 capture a sound signal from an environment of the hearing aid 2. Each one of the microphones 5 converts the captured sound signal into a respective input audio signal that is fed to the signal processor 11. The signal processor 11 processes the input audio signals of the microphones 5, i.a., to provide a directed sound information, to perform noise reduction and to individually amplify different spectral portions of the audio signal based on audiogram data of the user to compensate for the user-specific hearing loss. Hereby, the signal processing performed by the signal processor 11 depends on a plurality of (e.g. more than 200) signal processing parameters that are set to specific values during fitting, i.e. during adapting the hearing aid 2 to the needs of the individual user. The signal processor 11 emits an output audio signal to the receiver 7. The receiver 7 converts the output audio signal into a processed sound signal that is emitted into the ear canal of the user.

The VAD module 13 generally detects the presence or absence of voice (independent of a specific speaker) in the captured audio signal, whereas the OVD module 14 specifically detects the presence or absence of the user's own voice. By preference, modules 13 and 14 apply technologies of VAD and OVD, that are as such known in the art, e.g. from U.S. patent publication No. 2013/0148829 A1 or international patent publication WO 2016/078786 A1.

During recognized own-voice intervals, i.e. periods of time in which OVD module 14 detects the presence of the user's own in the input audio signal, the analysis unit 15 analyzes the input audio signal to determine certain acoustic features of the own voice of the user. E.g., the pitch F of the user's voice and the voice level V are determined. Moreover, the analysis unit 15 determines the noise level N (i.e. the sound level of the sound contained in the input audio signal that is not related to the user's own voice).

The hearing aid 2 and the hearing app 3 exchange data via a wireless link 17, e.g. based on the Bluetooth standard. To this end, the hearing app 3 accesses a wireless transceiver (not shown) of the smartphone 4, in particular a Bluetooth transceiver, to send data to the hearing aid 2 and to receive data from the hearing aid 2. In particular, during operation of the hearing aid 2, the VAD module 13 sends signals indicating the detection or non-detection of general voice activity to the hearing app 3. Likewise, the OVD module 15 sends signals indicating the detection or non-detection of own voice activity to the hearing app 3. Moreover, the analysis unit 15 sends the determined values of the pitch F, the voice level V and the noise level N to the hearing app 3.

The hearing app 3 includes a control unit 18 that is configured to compare current values of the pitch F, the voice level V and the noise level N to predetermined reference values $F_0$, $V_0$ and $N_0$ and to adapt, independence of the result of the comparison, a predefined subset of the signal processing parameters during own-voice intervals in order to alter the sound of the processed own-voice as is perceived by the user in order to change the emotional state of the user. In the present example, the signal processing parameters to be adapted include:

a pitch shift parameter S specifying a shift of the pitch F of the captured sound signal during own-voice intervals; e.g. the pitch shift parameter S specifies a factor by which the signal controller 11 increases (or decreased in the case of S<1) the input audio signal in frequency;

a compression ratio parameter R specifying a knee point in a dynamic compression curve of a compression algorithm implemented in the signal controller 11; dynamic compression results in narrowing the dynamic range of the user's own-voice signal by reducing the level of loud sounds, in relation to the level of soft sounds, to make the voice signal sound more intense; the compression may also be an "inverse compression", i.e. an extension or widening of the dynamic range;

a cut-off frequency C of a high-pass filter implemented in the signal controller 11; and a noise reduction parameter O specifying an intensity of a noise reduction performed by the signal controller 11.

Figure 2:
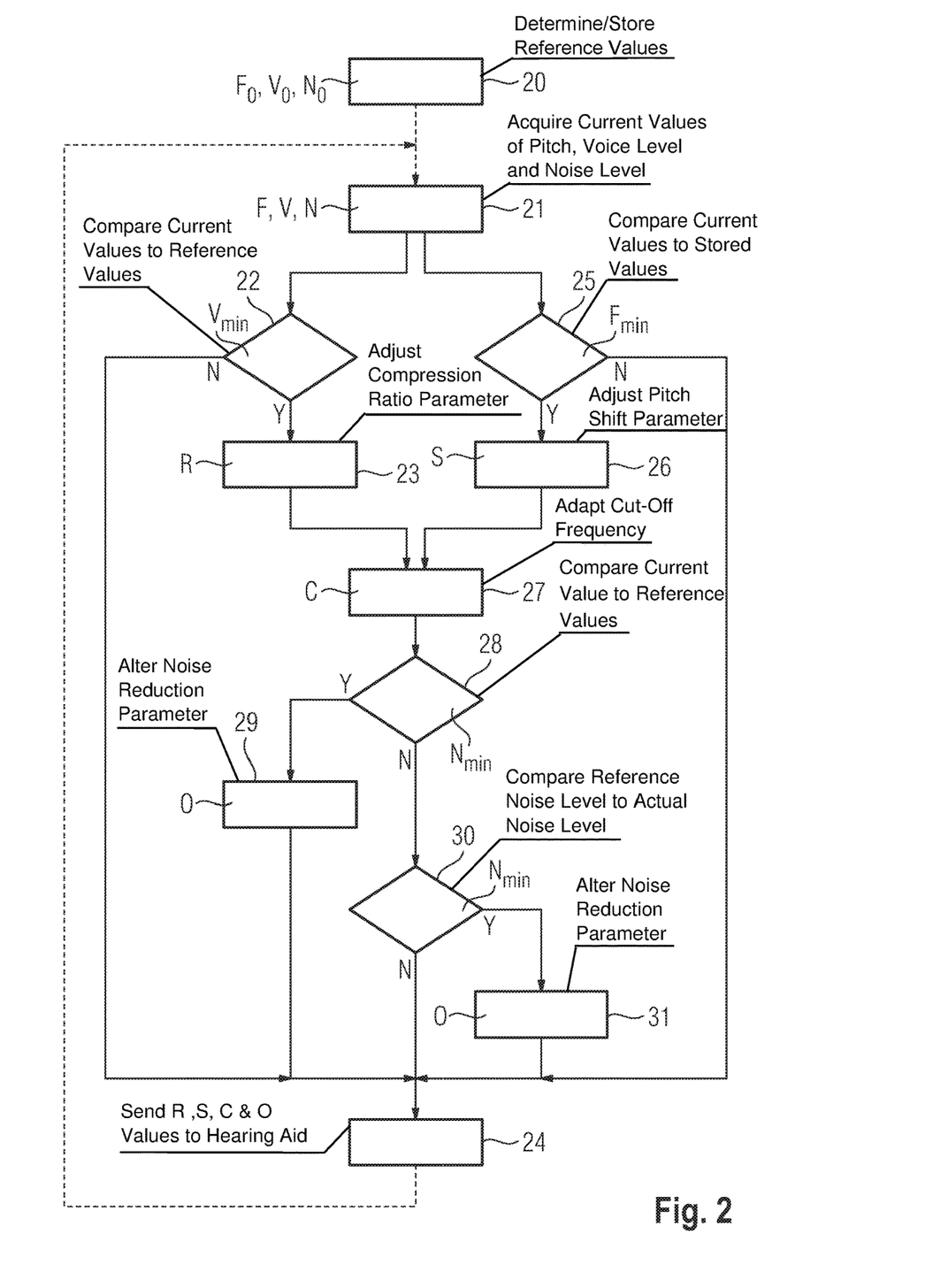
FIG. 2 is a flow chart showing a method for operating the hearing instrument of FIG. 1.

In detail, the system 1 automatically performs the method described hereafter with respect to FIG. 2.

In a first step 20, preceding the real life use of the hearing aid 2, the control unit 18 starts a training period of, e.g., ca. 5 min, during which the control unit 18 determines the reference values $F_0$, $V_0$ and $N_0$. The reference values $F_0$, $V_0$ and $N_0$ are determined by averaging over values of pitch F, the voice level V and the noise level N that have been recorded by the analysis unit 15 during the training period. The training period is selected so that, for its duration, the noise level N has normal (and, for the user, acceptable) values and the user is in a neutral emotional state (desired state). Thus, the reference values $F_0$, $V_0$ and $N_0$ constitute desired values of pitch F, the voice level V and the noise level N. As an alternative, the averaging mentioned above may be performed by the analysis unit 15. In this embodiment, the reference values $F_0$, $V_0$ and $N_0$ are provided by the analysis unit 15.

The step 20 is started on request of the user. After having determined the reference values $F_0$, $V_0$ and $N_0$, the control unit 18 persistently stores the reference values $F_0$, $V_0$ and $N_0$ in the memory of the smartphone 4.

In the real life use of the hearing aid 2, in a step 21 during own-voice intervals subsequent to the training period, the analysis unit 15 acquires current values of the pitch F of the user's voice, the voice level V and the noise level N and sends these values to the control unit 18.

The control unit 18 determines the emotional state of the user by applying a three-step criterion on the current values of the pitch F, the voice level V and the noise level N.

To this end, in a first comparison step 22, the control unit 18 compares the current values of the voice level V with the reference value $V_0$. If, for a given time interval (of, e.g., 10 to 15 seconds), the current values of the voice level V exceed the reference value $V_0$ by more than a predetermined threshold $V_{min}$ ($V-V_0 > V_{min}$), then the control unit 18 decides that the emotional state of the user is characterized by a high level of arousal. In this case (Y), the control unit proceeds to a step 23 as subsequently defined. Otherwise (N), the control unit 18 proceeds to a step 24, in which this thread of the method is terminated.

In a second comparison step 25 (being performed in parallel to step 22), the control unit 18 compares the current values of the pitch F with the reference value $F_0$. If, for the time interval specified above, the current values of the pitch F fall below the reference value $F_0$ by more than a threshold $F_{min}$ ($F-F_0 < -F_{min}$; with $F_{min} > 0$), then the control unit 18 decides that the emotional state of the user is characterized by a low valence. In this case (Y), the control unit proceeds to step 26 as subsequently defined. Otherwise (N), the control unit 18 proceeds to the step 24, in which this thread of the method is terminated.

In step 23, i.e. if a high level of arousal was recognized, the control unit 18 slightly increases the compression ratio parameter R by a predetermined amount, resulting in lowering the knee point of the dynamic compression curve.

In step 26, i.e. if a low valence was recognized, the control unit 18 slightly increases the pitch shift parameter S by a predetermined step size.

Subsequent to one of steps 23 and 26, the control unit 18 adapts the cut-off frequency C according to a predetermined function depending on the deviation $V-V_0$ of the voice level V and its reference value $V_0$ and the deviation $F-F_0$ of the pitch F and its reference value $F_0$ (step 27).

Thereafter, in a third comparison step 28, the control unit 18 tests whether the current noise level N overshoots the reference value $N_0$. If, for the time interval specified above, the current values of the noise level N exceed the reference value $N_0$ by more than a threshold $N_{min}$ ($N-N_0 > N_{min}$), then (Y) the control unit 18 proceeds to a step 29, in which it alters the noise reduction parameter O so to intensify the noise reduction.

Otherwise (N), in a step 30, the control unit 18 tests whether the current noise level N undershoots the reference value $N_0$. If, for the time interval specified above, the current values of the noise level N fall below the reference value $N_0$ by more than a threshold $N_{min}$ ($N-N_0 < -N_{min}$), then (Y) the control unit 18 proceeds to a step 31, in which it alters the noise reduction parameter O so to reduce the noise reduction.

Subsequent to one of steps 29 and 31, and if step 30 returns a negative test result (N), i.e. if the current values of the noise level N are found not to undershoot the reference value $N_0$, the control unit 18 proceeds to step 24.

In step 24, the control unit 18 sends the current values of the compression ratio parameter R, the pitch shift parameter S, cut-off frequency C and the noise reduction parameter O to the hearing aid 2 so that the signal processing performed by the signal processor 11 during own-voice intervals is controlled by these current parameter values. If at least one of the parameters R, S, C and O has been adapted by the control unit 18, the adaptation will manipulate the sound of the own voice as provided to the user and will, thus, influence the emotional state of the user.

In order to iteratively approximate the user's emotional state to the desired state, the control unit 18 repeats the method according to steps 21 to 31 in regular intervals, wherein said intervals are selected so to provide sufficient time for a reaction of the user to the altered parameter settings in the hearing aid 2. In each iteration step, the adaptation step size is sufficiently small so that the user will not become aware of the altered signal processing to evoke an unconscious reaction of the user. Alternatively, in order to achieve the same effect, the hearing aid 2 may slowly fade between previous and new parameter settings.

Parallel to performing the steps 21 to 31, the control unit 18 slowly approaches the values of the compression ratio parameter R, the pitch shift parameter S, cut-off frequency C and the noise reduction parameter O to predetermined default values, thus ensuring that the manipulations to the normal signal processing in the hearing aid 2 are reduced to a minimum needed (with respect to both their amount and duration).

In a variation of the first comparison step 22 of the method shown in FIG. 2, the control unit 18 compares the relation V/N of the voice level V and the noise level N with a corresponding reference value $V_0/N_0$. In this case, the method proceeds to step 23 if the current values of said relation V/N exceed the reference value $V_0/N_0$ by more than a predetermined threshold $V'_{min}$ (V/N−$V_0/N_0$>$V'_{min}$). The consideration of the relation V/N (instead of the voice level V) helps to better distinguish alterations of the voice level V that are caused by the emotional state of the user from those alterations of the voice level V that are caused by external circumstances, such as a noisy environment.

In further examples of the invention, the analysis unit 15 is configured to determine, by analysis of the input audio signal during own-voice-intervals, a temporal modulation (variation) of the voice level and/or the pitch F or a variable characterizing the rhythm of speech. In this case, the control unit 18 additionally considers these quantities in the decision whether or not and how to adapt the compression ratio parameter R, the pitch shift parameter S and the cut-off frequency C. In other variations of the invention, the control unit 18 further adapts the directional character of the processed audio signal and/or an intensity of pitch inflection when processing the input audio signal during own-voice intervals. Here, the term pitch inflection denotes a method in which the pitch of the user's own voice is rapidly modified at the beginning of each of the user's utterances, i.e. at the beginning of each of the own-voice-intervals in order to intensify or reduce intonation in the processed user's own voice. In particular, pitch inflection is used to make the user's voice sound more happy and to change the user's emotion accordingly.

Figure 3:
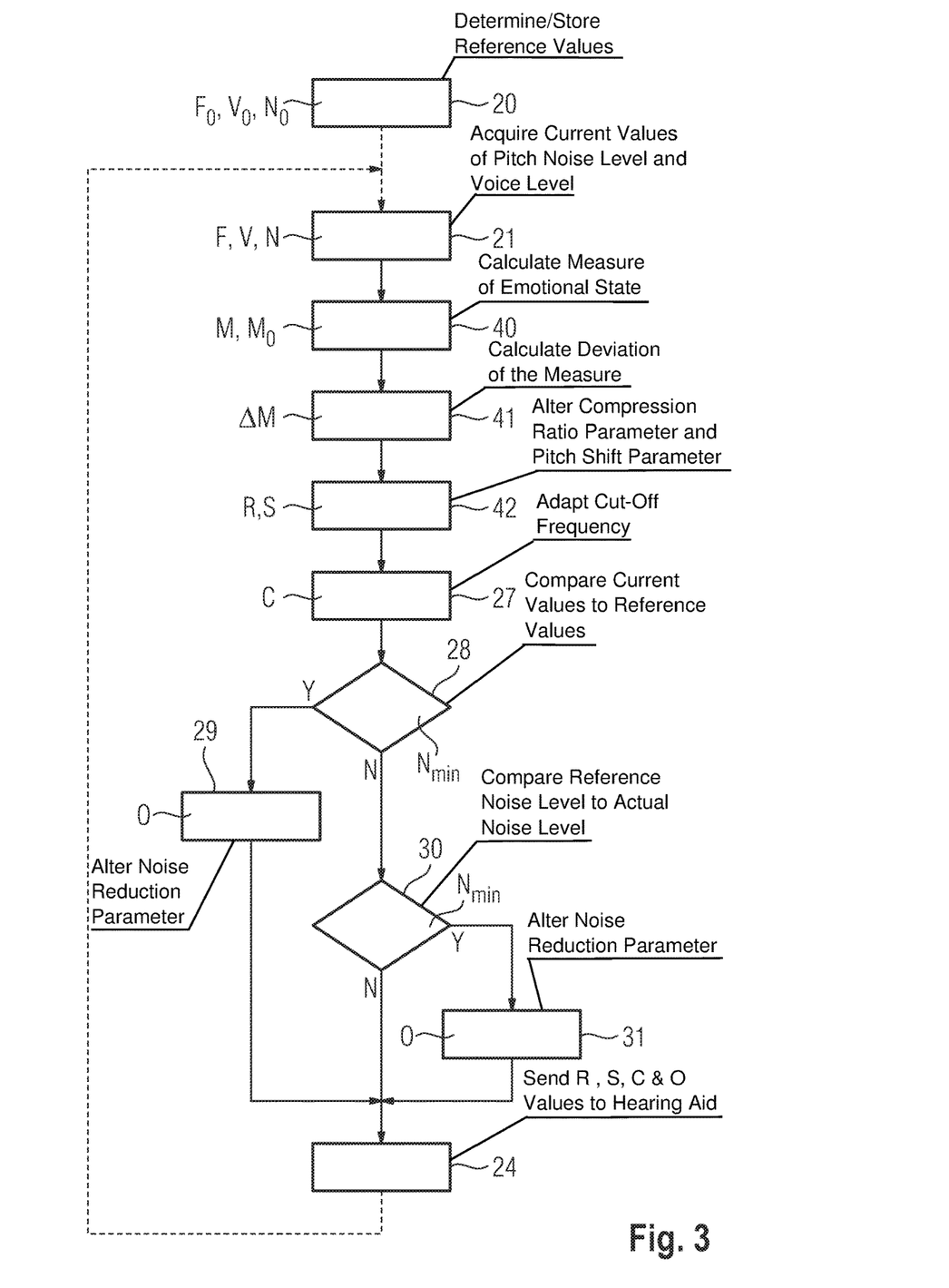
FIG. 3 is a flow chart showing a alternative embodiment of the method for operating the hearing instrument.

In another example, the control unit 18 is configured to conduct a method according to FIG. 3. Steps 20, 21, 24 and 27 to 31 of this method resemble the same steps of the method shown in FIG. 2.

The method of FIG. 3 deviates from the method of FIG. 2 in that, in a step 40 (following step 21), the control unit 18 calculates a measure M of the emotional state the user. As an example, the measure M may be defined as a vector of the deviation V−$V_0$ of voice level V and its reference value $V_0$ and the deviation F−$F_0$ of pitch F and its reference value $F_0$ (M={(V−$V_0$); (F−$F_0$)}). Hereby, the deviation V−$V_0$ is chosen for being indicative of the level of arousal of the user, whereas the deviation F−$F_0$ is chosen for being indicative of the valence of the emotional state of the user. The control unit 18 persistently stores the values of the measure M in the memory of the smartphone 4 as part of a data logging function. The stored values of the measure M are stored for a later evaluation by an audio care professional.

In a subsequent step 41, the control unit 18 calculates a deviation ΔM of the measure M from its desired value $M_0$={0;0}. In a simple yet effective embodiment, the deviation ΔM is defined as the vector length of the measure M.

In a step 42, the control unit 18 alters the compression ratio parameter R and the pitch shift parameter S so to iteratively minimize the deviation ΔM, using a Gradient descent optimization algorithm, i.e. the parameters R and S are altered (e.g. by a given step size within a two-dimensional space of the parameters R and S) so that a maximum decrease of the deviation ΔM is achieved.

Subsequent to step 42, the control unit 18 executes steps 27 to 31 and step 24 as described with respect to FIG. 2.

In a variation of the method of FIG. 3, the measure M is defined in dependence of the relation V/N and the pitch F (M={(V/N−$V_0/N_0$); (F−$F_0$)}). In a further variation, the dependence of the measure M of voice level V and the pitch F is defined as a non-linear mathematic function.

Figure 4:
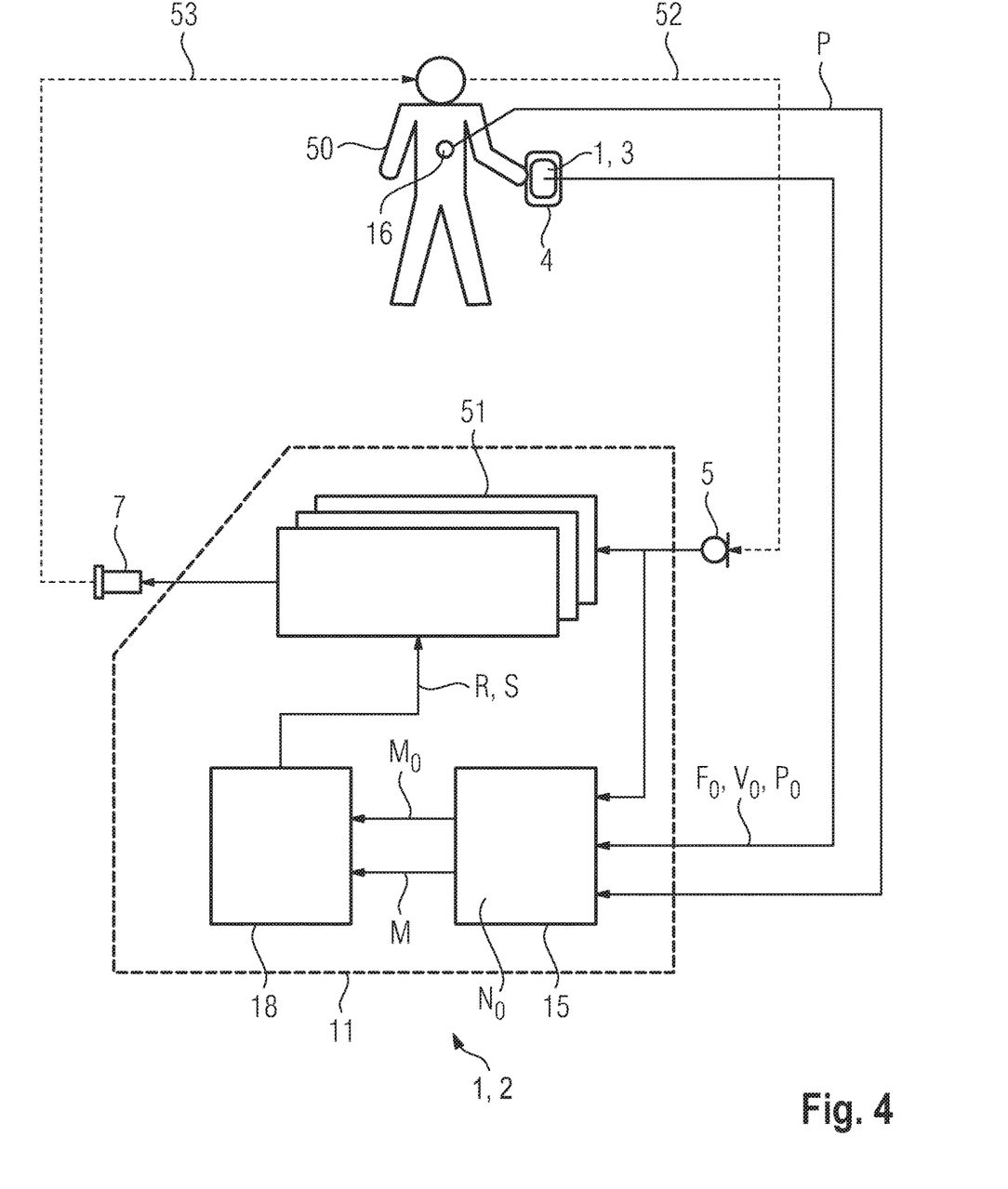
FIG. 4 is a block diagram of an analysis unit and a control unit of the hearing system in which a further embodiment of the method is implemented.

FIG. 4 shows, in a schematic block diagram, another embodiment of the hearing system 1. Here, different from the embodiment of FIG. 1, the control unit 18 is implemented in the hearing aid 2, as a functional part of the signal processor 11. Moreover, in the embodiment of FIG. 4, the bio sensor 16 is arranged external to the hearing aid 2, e.g. as a separate body-worn sensor. In the embodiment of FIG. 4, the bio sensor 16 is a pulse sensor that may be attached to the chest or wrist of the user 50.

As also shown in FIG. 4, the signal processor 11 contains a plurality of signal processing modules 51, e.g. as software modules. The signal processing modules 51 provide signal processing functions such as noise reduction, frequency-dependent sound amplification, pitch shift, spectral filtering, dynamic compression, etc. The operation of the signal processing modules 51 is controlled by a plurality of signal processing parameters as mentioned before, e.g. including the pitch shift parameter S and the compression ratio parameter R. As mentioned before, values of the pitch shift parameter S and the compression ratio parameter R are provided by the control module 18.

As described before, the signal processor 11 applies voice activity detection and own voice detection to an input audio signal provided by the microphones 5 (of which, for sake of simplification, only one is shown in FIG. 4). Also, for sake of simplification only, the corresponding modules 13 and 14 are not shown in FIG. 4.

FIG. 4 shows a use case of the hearing system 1, in which the user 50 speaks. In this case, the sound signal captured by the microphones 5 contains the user's own voice, as is indicated in FIG. 4 by a dashed line 52. In the signal processor 11, the corresponding input audio signal (containing an electric representation of the user's own voice) is routed to the signal processing modules 51 to be processed in dependence of the signal processing parameters. Moreover, the input audio signal is fed to the analysis module 15 which analyses the input audio signal, as described before, to determine current values of the pitch F, the voice level V and the noise level N of the user's 50 own voice.

Moreover, in the embodiment according to FIG. 4, the analysis module 15 receives current values of the user's 50 pulse frequency P from the bio sensor 16.

In a step similar to step 40 of the method of FIG. 3, the analysis module 15 determines the measure M of the emotional state of the user 50. Here, for example, the measure M may be determined using a predetermined mathematical function of the pitch F, the voice level V, the noise level N and the pulse frequency P (M=M(F,V,N,P). Using the same mathematical function, and based on the reference values $F_0$, $V_0$, $N_0$ as well a reference value $P_0$ of the pulse frequency P, the analysis module 15 also determines the desired value $M_0$ of the measure M ($M_0$=M($F_0$,$V_0$,$N_0$,$P_0$)). In the embodiment of FIG. 4, the reference values $F_0$, $V_0$ and $P_0$ are provided by hearing app 3. Preferably, these reference values $F_0$, $V_0$ and $P_0$ can be altered by the user 50 via the smartphone 4. In contrast, the reference value $N_0$ may be preset (e.g. by an audiologist during fitting) as constant in the analysis module 15. As an alternative, all reference values $F_0$, $V_0$, $N_0$, $P_0$ may be predetermined as constants, e.g. by an audiologist during fitting (such that they cannot be altered by the user 50).

In step similar to steps 41 and 42 of FIG. 3, the control unit 18 calculates the deviation ΔM of the measure M from its desired value $M_0$ and alters the compression ratio parameter R and the pitch shift parameter S so to iteratively minimize the deviation ΔM. To this end, the control unit 18 may use a Gradient descent optimization algorithm as described before.

Based on altered values of the compression ratio parameter R and the pitch shift parameter S, the signal processing modules 51 process the user's 50 own voice in a modified way. The processed signal (containing the thus modified own voice of the user 50) is fed back to user 50 via the receiver 7, as is indicated in FIG. 4 by a dashed line 53. The modified perception of his own voice influences the emotional state of the user 50 which, in turn, influences the user's own voice. Thus, a closed control loop is formed by the hearing system 1 and the user 50 allowing to approach the user's emotional state towards a target emotional state represented by the reference value $M_0$.

As will be appreciated by persons skilled in the art, numerous variations and/or modifications may be made to the invention as shown in the specific examples without departing from the spirit and scope of the invention as broadly described in the claims. The present examples are, therefore, to be considered in all aspects as illustrative and not restrictive.

The following is a summary list of reference numerals and the corresponding structure used in the above description of the invention:
1 (hearing) system
2 hearing aid
3 hearing app
4 smartphone
5 microphones
7 receiver
9 battery
11 signal processor
12 voice recognition unit
13 voice activity detection module (VAD module)
14 own voice detection module (OVD module)
15 analysis unit
16 bio sensor
17 wireless link
18 control unit
20-31 step
40-42 step
50 user
51 signal processing module
52 line
53 line
ΔM deviation
C cut-off frequency
F pitch
$F_0$ reference value
$F_{min}$ threshold
N noise level
$N_0$ reference value
$N_{min}$ threshold
M measure
$M_0$ desired value
O noise reduction
P pulse frequency
$P_0$ reference value
R compression ratio parameter
S pitch shift parameter
V voice level
$V_0$ reference value
$V_{min}$ threshold

The invention claimed is:

1. A method for operating a hearing system having a hearing instrument that is worn in or at a ear of a user, which comprises the following steps of:
capturing a sound signal from an environment of the hearing instrument;
processing a captured sound signal in dependence of a set of signal processing parameters;
analyzing the captured sound signal to recognize own-voice intervals, in which the user speaks;
analyzing the captured sound signal for at least one acoustic feature of an own voice of the user and/or analyzing a signal of at least one bio sensor, the at least one bio sensor measuring at least one non-acoustic vital function of the user;
determining, from the at least one acoustic feature of the own voice of the user and/or the at least one non-acoustic vital function of the user, a measure of an emotional state of the user;
testing the measure of the emotional state with respect to a predefined criterion;
adapting a value of at least one of the signal processing parameters, within the own-voice intervals, to change the emotional state if the predefined criterion is fulfilled, wherein the predefined criterion having a desired value of the measure of the emotional state;
performing the testing step to include a determination of a deviation of the measure of the emotional state with respect to the desired value;
adapting a value of at least one of the signal processing parameters so that the deviation is reduced; and
outputting a processed sound signal to the user.

2. The method according to claim 1, which further comprises:
further analyzing the captured sound signal for at least one of the following environmental acoustic features:
a sound level of the captured sound signal;
a noise level or a signal-to-noise ratio;
a reverberation time; and
a presence of speakers different from the user; and
determining the measure of the emotional state in further dependence on at least one environmental acoustic feature and/or a temporal variation thereof.

3. The method according to claim 1, wherein the at least one signal processing parameter that is adapted is selected from at least one of
a parameter of a noise reduction algorithm;
a parameter of an algorithm adapting a pitch of the captured sound signal;
a parameter of an algorithm adapting a dynamic range of the captured sound signal;
a parameter for switching between binaural or monoaural sound processing;
a parameter of a beamforming algorithm; and
a parameter of an algorithm adapting spectral energy of the captured sound signal.

4. The method according to claim 1, wherein the at least one acoustic feature of the own voice of the user for which the captured sound signal is analyzed is selected from at least one of:
a voice level;
formant frequencies;
a pitch;
a frequency distribution; and
a speed or rhythm of speech.

5. The method according to claim 1, wherein the at least one non-acoustic vital function of the user measured by the at least one bio sensor is selected from at least one of:
a pulse frequency;
an oxygen content of blood;
blood pressure;
brain activity;
muscle activity;
a motion of the user;
skin conductivity; and
body temperature.

6. The method according to claim 5, wherein the at least one non-acoustic vital function of the user measured by the at least one bio sensor is a frequency and/or amplitude of a head movement of the user.

7. A method for operating a hearing instrument that is worn in or at an ear of a user, which comprises the following steps of:
capturing a sound signal from an environment of the hearing instrument;
processing a captured sound signal in dependence of a set of signal processing parameters;
analyzing the captured sound signal to recognize own-voice intervals, in which the user speaks;
analyzing the captured sound signal for at least one acoustic feature of an own voice of the user and/or analyzing a signal of at least one bio sensor, the at least one bio sensor measuring at least one non-acoustic vital function of the user;
testing the at least one acoustic feature of the own voice of the user and/or the at least one non-acoustic vital function of the user, with respect to a predefined criterion;
adapting a value of at least one of the signal processing parameters, within the own-voice intervals, to change an emotional state if the predefined criterion is fulfilled, wherein the predefined criterion having a desired value of the at least one acoustic feature of the own voice of the user and/or the at least one vital function of the user;
performing the testing step to include a determination of a deviation of the at least one acoustic feature of the own voice of the user and/or the at least one vital function of the user with respect to the desired value;
adapting a value of at least one of the signal processing parameters so that the deviation is reduced; and
outputting a processed sound signal to the user.

8. The method according to claim 7, which further comprises:
analyzing the captured sound signal for at least one environmental acoustic feature selected from the group consisting of:
a sound level of the captured sound signal;
a noise level or a signal-to-noise ratio;
a reverberation time; and
a presence of speakers different from the user; and
testing the at least one environmental acoustic feature, with respect to the predefined criterion.

9. A hearing system with a hearing instrument to be worn in or at an ear of a user, the hearing instrument comprising:
an input transducer disposed to capture a sound signal from an environment of the hearing instrument;
a signal processor disposed to process a captured sound signal in dependence of a set of signal processing parameters;
an output transducer disposed to emit a processed sound signal into the ear of the user;
a voice recognition unit configured to analyze the captured sound signal to recognize own-voice intervals, in which the user speaks;
at least one bio sensor measuring at least one non-acoustic vital function of the user;
an analysis unit configured to analyze the captured sound signal for at least one acoustic feature of an own voice of the user and/or to analyze a signal of said at least one bio sensor;
a controller configured to determine, from the at least one acoustic feature of the own voice of the user and/or the at least one non-acoustic vital function of the user, a measure of an emotional state of the user, wherein the controller is configured to:
test the measure of the emotional state with respect to a predefined criterion; and
adapt a value of at least one of the signal processing parameters, within the own-voice intervals, to change the emotional state if the predefined criterion is fulfilled, wherein the predefined criterion includes a desired value of the measure of the emotional state;
determine a deviation of the measure of the emotional state with respect to the desired value; and
adapt the value of the at least one signal processing parameter so that the deviation is reduced.

10. The hearing system according to claim 9, wherein:
said analysis unit is configured to further analyze the captured sound signal for at least one of the following environmental acoustic features:
a sound level of the captured sound signal;
a noise level or a signal-to-noise ratio;
a reverberation time; and
a presence of speakers different from the user; and said controller is configured to determine the measure of the emotional state in further dependence of the at least one environmental acoustic feature and/or a temporal variation thereof.

11. A hearing system with a hearing instrument to be worn in or at the ear of a user, the hearing instrument comprising:
- an input transducer disposed to capture a sound signal from an environment of the hearing instrument;
- a signal processor disposed to process a captured sound signal in dependence of a set of signal processing parameters;
- an output transducer disposed to emit a processed sound signal into the ear of the user;
- a voice recognition unit configured to analyze the captured sound signal to recognize own-voice intervals, in which the user speaks;
- at least one bio sensor measuring at least one non-acoustic vital function of the user;
- an analysis unit configured to analyze the captured sound signal for at least one acoustic feature of an own voice of the user and/or to analyze a signal of said at least one bio sensor;
- a controller configured to:
  - test the at least one acoustic feature of the own voice of the user and/or the at least one non-acoustic vital function of the user, with respect to a predefined criterion;
  - adapt a value of at least one of the signal processing parameters, within the own-voice intervals, to change the emotional state if the predefined criterion is fulfilled, wherein the predefined criterion having a desired value of the at least one acoustic feature of the own voice of the user and/or the at least one vital function of the user;
  - determine a deviation of the at least one acoustic feature of the own voice of the user and/or the at least one vital function of the user with respect to the desired value; and
  - adapt a value of the at least one signal processing parameter so that the deviation is reduced.

12. The hearing system according to claim 11, wherein:
said analysis unit is configured to analyze the captured sound signal for at least one environmental acoustic feature selected from the group consisting of:
- a sound level of the captured sound signal;
- a signal-to-noise ratio;
- reverberation time; and
- presence of speakers different from the user; and said controller is configured to test the at least one environmental acoustic feature with respect to the predefined criterion.

* * * * *